United States Patent
Yamazaki et al.

(10) Patent No.: US 7,048,788 B2
(45) Date of Patent: May 23, 2006

(54) SHIP BOTTOM PAINT USING COAL ASH AND DIATOMACEOUS EARTH

(76) Inventors: Shunichi Yamazaki, 3-1-2 Kogandori, Suwa-shi (JP); Minoru Okuda, 4120-1 Satoyamabe, Matsumoto-city, Nagano (JP)

( * ) Notice: Subject to any disclaimer, the term of this patent is extended or adjusted under 35 U.S.C. 154(b) by 0 days.

(21) Appl. No.: 10/913,133

(22) Filed: Aug. 5, 2004

(65) Prior Publication Data

US 2006/0005741 A1    Jan. 12, 2006

Related U.S. Application Data

(60) Provisional application No. 60/492,797, filed on Aug. 5, 2003.

(30) Foreign Application Priority Data

Oct. 24, 2003    (JP) .............................. 2003-365020

(51) Int. Cl.
C09D 5/14    (2006.01)
C09D 5/16    (2006.01)
A01N 59/00    (2006.01)
A01N 63/00    (2006.01)

(52) U.S. Cl. ................... 106/15.05; 106/482; 106/483; 106/681; 106/706; 424/78.09; 424/93.51; 424/600; 424/682

(58) Field of Classification Search ............. 106/15.05, 106/706, 482, 483, 681; 424/78.09, 600, 424/682, 93.51, 609
See application file for complete search history.

(56) References Cited

U.S. PATENT DOCUMENTS

| | | | | |
|---|---|---|---|---|
| 4,055,639 A | * | 10/1977 | Hirose et al. | 514/166 |
| 4,055,640 A | * | 10/1977 | Hirose et al. | 514/166 |
| 4,082,884 A | * | 4/1978 | De Long | 442/123 |
| 4,273,833 A | * | 6/1981 | De Long | 114/361 |
| 4,378,402 A | * | 3/1983 | Below | 442/19 |
| 5,324,525 A | * | 6/1994 | Sakuma et al. | 424/602 |
| 5,449,553 A | * | 9/1995 | Griffith | 428/332 |
| 5,593,732 A | * | 1/1997 | Griffith | 427/407.1 |
| 6,069,161 A | * | 5/2000 | Reuther et al. | 514/372 |
| 6,294,006 B1 | * | 9/2001 | Andou | 106/14.05 |
| 6,299,854 B1 | * | 10/2001 | Henmi et al. | 423/700 |
| 6,458,878 B1 | * | 10/2002 | Tsuboi et al. | 524/432 |
| 2003/0166765 A1 | | 9/2003 | Sugihara | |
| 2005/0014881 A1 | * | 1/2005 | Weitzel et al. | 524/442 |

FOREIGN PATENT DOCUMENTS

| | | | | |
|---|---|---|---|---|
| FR | 2420512 A | * | 10/1979 | |
| GB | 2117753 A | * | 10/1983 | |
| GB | 2306491 A | * | 5/1997 | |
| JP | 2-222643 A | * | 9/1990 | |
| JP | 09-16555 A | | 6/1997 | |
| JP | 2000-226554 A | * | 8/2000 | |
| JP | 2002-253973 A | | 9/2002 | |
| WO | WO 02/40609 A1 | | 5/2002 | |

* cited by examiner

*Primary Examiner*—Anthony J. Green
(74) *Attorney, Agent, or Firm*—Christensen O'Connor Johnson Kindness PLLC

(57) ABSTRACT

A ship bottom paint additive to prevent or reduce marine life attachment to the bottoms of ships, and ship bottom paint comprises a mixture of coal ash and diatom earth or beer yeast diatom earth wherein the coal ash is preferably fly ash and the diatom earth or beer yeast diatom earth is preferably a dry powder. The additive is a mixture may have a weight ratio within the range of about 3:1 to 7:1, and may be comprised of about 2.25–10% by weight coal ash and about 0.375–5% by weight diatom earth or beer yeast diatom earth.

26 Claims, No Drawings

SHIP BOTTOM PAINT USING COAL ASH AND DIATOMACEOUS EARTH

CROSS-REFERENCES TO RELATED APPLICATIONS

This application claims the benefit of U.S. Provisional Application No. 60/492,797, filed Aug. 5, 2003, the benefit of which is hereby claimed under 35 U.S.C. § 119 and is incorporated herein by reference.

FIELD OF THE INVENTION

This invention concerns ship bottom paint additives to reduce shellfish and other marine life attaching to ship bottoms and other marine structures, and ship bottom paints that contain this particular additive.

BACKGROUND OF THE INVENTION

Shellfish and other marine life that attach to the bottoms of ships, marine structures, and various equipment and devices used in the ocean decrease the functionality of these structures over time. In an effort to address this problem, several types of paints have been suggested to prevent shellfish and other marine life attachment.

In the past, paint with organotin compounds such as tribytyltine were proposed and used to prevent shellfish attachment. However, marine contamination due to the organotin compounds has become problematic in recent years, and the use of such paints has been banned.

One composition of non-toxic antifouling coating is disclosed by U.S. Pat. No. 5,958,116. This composition is comprised of room temperature-cured silicone rubbers, silicone oil, and hydrophobic fumed silicon.

Other currently available technologies require expensive materials, and often do not yield satisfactory results. Japanese Published Unexamined Application Report Hei 11-349974 proposes algae-resistant/shellfish-resistant paint made by evenly mixing inorganic antimicrobial agents including silver and/or copper with water-repellant paint. Japanese Published Unexamined Application Report Hei 8-218004 proposes an anti-algae-and-shellfish-attachment paint that contains far-infrared ray radioactive ingredients such as ceramics, minus-ion radioactive materials like tourmaline, and garlic powder. Japanese Published Unexamined Application Report 2001-29818 suggests bio-fouling resistant paint made of conductive paint mixed with magnetic materials.

SUMMARY OF THE INVENTION

The present invention provides a ship bottom paint additive using inexpensive materials to prevent or reduce shellfish or other marine life attachment to the bottoms of ships, and ship bottom paints with this particular additive.

The ship bottom paint additive of the present invention is prepared from fly ash ground at an average of 1–12 μm granularity mixed with dry diatomaceous earth or beer yeast diatomaceous earth of similar granularity, the mixture having a weight ratio within the range of 3:1 to 7:1. This invention also includes ship bottom paint that has the above-described additive added as 3–10% by weight of the paint solid content.

This additive invention is highly effective in preventing or reducing the attachment of shellfish and algae to ship bottoms and marine structures. In addition, this invention also provides an inexpensive solution to waste disposal processing as fly ash and diatomaceous earth or beer yeast diatomaceous earth are all process waste materials, and these materials form the ingredients of the additive of the present invention. Furthermore, as these two materials are both relatively light in weight, the painted layer is also relatively light in weight and exerts a minimal impact on the painted ship.

DETAILED DESCRIPTION OF THE PREFERRED EMBODIMENT

The present invention concerns the use of coal ash, which is produced in coal-fired power stations by burning pulverized coal. The coal ash is the residual from the burned coal. Coal ash takes two general forms, fly ash and bottom ash.

Bottom ash is the coal ash which is initially burnt red-hot and then dropped into a water-filled hopper at the bottom of the boiler. Thereafter, the bottom ash is crushed and screened according to size. Bottom ash is chemically stable, has a porous structure and, in composition, typically includes the following:

$SiO_2$—51%–64%;
$Al_2O_3$—17%–27%;
$Fe_2O_3$—3%–11%;
$MgO$—0.9%–3%; and
$CaO$—1.9%–9%.

Fly ash refers to fine ash particles formed from the mineral matter in coal and present in the chimney fumes of coal-fired boilers such as coal-fired power plants. Fly ash particles can be collected with electrostatic precipitators. Generally, fly ash particles are spherical in shape and have a pozzolanic effect, meaning that when mixed with water, the fly ash will chemically react with calcium hydroxide to form compounds with cementitious properties. Silica and alumina typically form the major components of fly ash, accounting for approximately 70–80% by weight. Fly ash also contains small amounts of iron oxide, Mg, Ca, P and Ti oxides, trace elements, non-crystal (glassy phase) materials that are generated when molten materials are cooled down rapidly, and crystal minerals such as quartz and mullite. It is also known for the inclusion of low-crystal allophane that is mainly composed of hydrated aluminum silicate.

In composition, fly ash typically includes the following:

$SiO_2$—44%–74%;
$Al_2O_3$—16%–39%;
$Fe_2O_3$—6%–22%;
$MgO$—0.2%–3%; and
$CaO$—0.1%–14.5%.

Generally speaking, the particle diameter of fly ash ranges from 1 to 200 μm with an average size of approximately 20 μm. The fly ash applied in the current invention is ground to an average particle size of about 1–12 μm. It is considered better if the particle size range is 1–8 μm, and a more preferable range is about 1–5 μm, with an even more preferable range of about 2–4 μm producing the best quality. The fly ash can be ground with a jet grinder. If the average granularity is less than 1 μm, the grinding cost becomes excessive and it is very difficult to mix the fly ash with paint. Conversely, if the average fly ash particle size is significantly greater than about 12 μm, the effectiveness of the additive may be reduced.

The dry powder of diatomaceous earth or beer yeast diatomaceous earth used in this invention is produced by drying diatomaceous earth or beer yeast diatomaceous earth used for beer fermentation, and grinding such earth into powder. The granularity of diatomaceous earth should be such that the powder can be well mixed with the fly ash used in this invention. Thus, the diatomaceous earth or beer yeast diatomaceous earth component of the current additive may have an average particle size of 1–12 μm, with the preferable range being about 3–10 μm.

The mixing ratio of fly ash and dry powder of diatomaceous earth or beer yeast diatomaceous earth may be from 3–7 to 1. A ratio of 4–6 to 1 is preferable, with 5 to 1 being more preferred. It is also known that the effectiveness of the present invention may be reduced if the ratio of fly ash to dry powder of diatomaceous earth or beer yeast diatomaceous earth is greater than about 7 to 1 or smaller than about 3 to 1.

Applicants' novel composition may include about 2.25–10% by weight coal ash, and desirably, fly ash. Applicants' composition may also include 0.375–5% by weight diatomaceous earth or beer yeast diatomaceous earth. Preferably, the applicant's composition includes about 2.5–8.33% by weight coal ash, desirably, fly ash, and about 0.5–1.67% by weight diatomaceous earth or beer yeast diatomaceous earth.

The ship bottom paint additive in this invention can be manufactured by mechanically mixing ground fly ash with dry diatomaceous earth or beer yeast diatomaceous earth powder using a mixing machine or by hand in a container. It is important that these two ingredients be sufficiently mixed together. The remainder of applicants' composition may be composed of silicon rubber or other similar material and color and other pigments.

By adding the above-described additive of this invention to ship bottom paint at about 3–10% by weight of the paint solid content, shellfish, algae, and other marine life attachment to the painted bottom of the ship can be decreased or perhaps even substantially prevented.

The effectiveness that can be achieved with this additive is not fully understood. Through trial and error, the applicants focused on allophone present in the fly ash and yeast that lives in the dry powder of beer yeast diatomaceous earth, mixed both components at the above-described mixing ratios, and discovered that a proper amount of mixed components blended into paint could yield a positive effect. Thus, the present invention also contemplates separating the allophane from the coal ash or fly ash and separating the beer yeast from the diatomaceous earth. The present invention also contemplates obtaining these active components from other sources.

The additive described herein may be used with the following paint types, among others: urethane paint, chlorinated rubber resin, epoxy resin such as vinyl tar epoxy corrosion-resistant paint, non-tar epoxy resin heavy duty corrosion-resistant paint, vinyl stain-resistant paint, acrylic stain-resistant paint, water-biodegradable paint or chlorinated polyolefin (chloride rubber) paint. The additive in this invention also may be mixed into primers for application.

In addition to the additive of the present invention, the paint may also contain one or more of the following ingredients: thermoplastic resin, various types of plastic agents, body pigments, color pigments, anti-corrosion pigments, solvents, hardening accelerator, viscosity modifier, thixo agent (anti-drip agent) and sedimentation-resistant agent.

The paints in this invention may be airless-sprayed to the ship bottom, including the water line, or applied by normal methods such as air spraying, brush painting or roller painting.

The paint volume used may vary depending on the type of ship, the number of paint layers, and other relevant factors. Generally speaking, the paint volume may be about 100–800 g/m$^2$, and the dried paint layer should be at a thickness of 30–500 μm, with 50–300 μm being more preferable.

The additive described herein can be used as part of a coating composition which is particularly useful for coating underwater structures such as ship hulls, ship water lines, port facility structures, buoys, pipelines, bridges, floats, oil field rigs, stationary fishing nets, and other marine structures. Applicants have found that its novel composition resists the build-up of marine organisms, including barnacles, ascidian, muscles, polyzoa, algae, etc. Moreover, applicants have found that their novel coating is substantially non-toxic and anti-fouling.

An example of the present invention is described below. This invention, however, is not limited to the following example.

Manufacturing of Ship Bottom Paint Additive:
  A. Manufacturing of Ground Fly Ash
    (1) Fly ash with an average granularity of 34.66 μm with the granularity distribution shown in Table 1 was ground in a jet grinder to an average granularity of 2.53 μm with the granularity distribution also shown in Table 1.

TABLE 1

| | Granularity distribution | | | | | | | | | |
|---|---|---|---|---|---|---|---|---|---|---|
| | 10% | 20% | 30% | 40% | 50% | 60% | 70% | 80% | 90% | 99% |
| Fly ash - raw material | 4.30 μm | 7.36 μm | 11.58 μm | 17.29 μm | 23.46 μm | 30.92 μm | 40.75 μm | 54.54 μm | 79.24 μm | 175.2 μm |
| Ground fly ash | 1.56 μm | 1.82 μm | 2.04 μm | 2.24 μm | 2.43 μm | 2.64 μm | 2.87 μm | 3.16 μm | 3.60 μm | 4.94 μm |

(2) Fly ash was ground in the same manner as described above in (1) to an average granularity of 4.17 μm, with a granularity distribution shown in Table 2.

TABLE 2

| | Granularity distribution | | | | | | | | | |
|---|---|---|---|---|---|---|---|---|---|---|
| | 10% | 20% | 30% | 40% | 50% | 60% | 70% | 80% | 90% | 99% |
| Ground fly ash | 3.66 μm | 4.42 μm | 5.01 μm | 5.53 μm | 6.03 μm | 6.55 μm | 7.13 μm | 7.87 μm | 9.03 μm | 12.0 μm |

(3) Fly ash was ground in the same manner as described above in (1) to an average granularity of 1.91 μm, with a granularity distribution shown in Table 3.

TABLE 3

| | Granularity | | | | | | | | | |
|---|---|---|---|---|---|---|---|---|---|---|
| | 10% | 20% | 30% | 40% | 50% | 60% | 70% | 80% | 90% | 99% |
| Ground fly ash | 1.62 μm | 1.89 μm | 2.12 μm | 2.34 μm | 2.56 μm | 2.79 μm | 3.06 μm | 3.40 μm | 3.90 μm | 5.39 μm |

B. Manufacturing of Beer Yeast Diatomaceous Earth

Used beer yeast diatomaceous earth that was obtained from beer manufacturers was dried for two weeks. The dried beer yeast diatomaceous earth was then ground to powder with an average granularity of 1–12 μm.

C. Additive Manufacturing Preparations

Fifty-weight of the ground fly ash described in (1) above was mixed with 10-weight of the beer yeast diatomaceous earth powder in a mixer to make ship bottom paint additive #1.

Seventy-weight of the ground fly ash described in (2) above was mixed with 10-weight of the beer yeast diatomaceous earth powder in the mixer to make ship bottom paint additive #2.

Forty-weight of the ground fly ash described in (3) above was mixed with 10-weight of the beer yeast diatomaceous earth powder in the mixer to make ship bottom paint additive #3.

Manufacturing of Ship Bottom Paint (1) Manufacturing of Paint A

The following ingredients were blended until they were evenly mixed: 600-weight of epoxy resin, 100-weight of rosin, 100-weight of talc, 100-weight of titanium dioxide, 50-weight of colcothar and 50-weight of thixo agent.

(2) Manufacturing of Paint B

The following ingredients were blended until they were evenly mixed: 700-weight of chloride rubber resin, 250-weight of colcothar, and 50-weight of thixo agent.

(3) Manufacturing of Paint C

The following ingredients were blended until they were evenly mixed: 700-weight of urethane resin, 250-weight of talc and 50-weight of thixo agent.

Paints A, B and C were respectively blended with the above-described ship bottom paint additives (1), (2) and (3) at the mixing ratios shown in Table 4. Using those blended ship bottom paints, the following test was performed.

Ship Bottom Paint Performance Test

This test was performed basically in accordance with Japan Industrial Standards (JIS) K 5630. In this regard, 300 mm×300 mm×3.2 mm sized hot rolled soft steel strips were cleaned with paint thinner to remove oil and other contaminants. After the strips were dried, they were sandblasted to remove mill-scale powder and rust, etc., resulting in a gray white finish surface with a roughness of 70S. These test strips were stored to avoid humidity, and SD Zinc 1000HA was brush-painted one time as an under-layer, according to JIS K 5400, at a thickness of 13.5 μm when dried. After the paint was dry, vinyl chloride resin paint for steel ship external shells was brush-painted 4 times over the under-layer according to JIS K 5634 to obtain a 105 μm dry layer. Finally, the above-described blended paints A, B, & C were respectively brush-painted two times to obtain a 40 μm dry layer each. In this way the shellfish attachment test strips were prepared. Using these test strips, ocean immersion tests were performed in the ocean according to JIS K 5630 for 6 months and one year, and the shellfish attachment conditions were measured.

Three test strips were created for each test paint. Average measurement results are shown in Table 4.

Shellfish Attachment Test

⊙: No attached shellfish or maximum of 4 pieces of attached shellfish

○: 5 to 10 pieces of attached shellfish

Δ: 11 to 20 pieces of attached shellfish

X: Numerous pieces of attached shellfish

TABLE 4

| | | Paint | Additive | | Shellfish attachment prevention performance |  |
|---|---|---|---|---|---|---|
| Test Strip Number | Type | Amount (weight %) | Additive Number | Additive amount (weight %) | 6 months | 1 year |
| 1 (comparison example) | A | 100 | | 0 | X | — |
| 2 | A | 95 | 1 | 5 | ⊙ | ⊙ |
| 3 | A | 93 | 1 | 7 | ⊙ | ⊙ |
| 4 | A | 97 | 1 | 3 | ⊙ | ○ |
| 5 (comparison example) | A | 98 | 1 | 2 | ○ | Δ |
| 6 (comparison example) | B | 99 | 2 | 1 | Δ | — |
| 7 | B | 93 | 2 | 7 | ⊙ | ⊙ |
| 8 | B | 95 | 2 | 5 | ⊙ | ⊙ |
| 9 (comparison example) | C | 90 | 3 | 13 | Δ | X |
| 10 | C | 92 | 3 | 3 | ⊙ | ○ |
| 11 | C | 94 | 3 | 6 | ⊙ | ⊙ |
| 12 (comparison example) | C | 98 | 3 | 11 | ○ | Δ |

As shown in the above test data, when Test Strips 5 and 6 with the additive at less than 3% by weight were used, we were able to obtain some expected level of effectiveness, but they were not considered satisfactory. When Test Strip 9, with the additive at more than 10% by weight, was used, only slight effectiveness was demonstrated, and it was also not satisfactory. Test Strips 2–4, 7–8, 10, and 11 had 3–10% by weight of the additive and demonstrated the effect of the additive of the present invention regardless of the paint types used. Test Strip 1 shows the test result of Paint A that had no amount of this additive. Based on these results, it can be concluded that paints that include the additive of the present invention at levels more or less than the range specified in this invention can show some degree of the effectiveness.

The present invention also contemplates utilizing coal ash as a component of building materials, in particular, structural building blocks. For example, fly ash or bottom ash can be used as a component of concrete building blocks, cement building blocks or ceramic building blocks.

As a further example of the present invention, coal ash can be used as a soil additive serving as both a fertilizer and also to improve the drainage capacity of the soil. For this use the coal ash can be mixed with 5–10% by weight diatomaceous earth.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A ship bottom paint additive comprising a mixture of coal ash and beer yeast diatomaceous earth, wherein the weight ratio of coal ash to beer yeast diatomaceous earth is within the range of about 3:1 to 7:1.

2. A ship bottom paint additive comprising a mixture of coal ash and beer yeast diatomaceous earth, wherein coal ash comprises about 2.25–10% by weight and beer yeast diatomaceous earth comprises about 0.375–5% by weight.

3. A ship bottom paint additive as recited in claim 1, wherein the coal ash comprises fly ash.

4. A ship bottom paint additive as recited in claim 1, wherein the beer yeast diatomaceous earth is in dry powder form.

5. A ship bottom paint additive as recited in claim 1, wherein coal ash and beer yeast diatomaceous earth are ground into an average granularity of about 1 to 12 μm.

6. A ship bottom paint additive as recited in claim 1, wherein coal ash is ground into an average granularity of about 2–4 μm, and beer yeast diatomaceous earth is ground into an average granularity of about 3–10 μm.

7. A ship bottom paint additive as recited in claim 1, further comprising diatomaceous earth.

8. A ship bottom paint additive as recited in claim 2, wherein the coal ash comprises fly ash.

9. A ship bottom paint additive as recited in claim 2, wherein the beer yeast diatomaceous earth is in dry powder form.

10. A ship bottom paint additive as recited in claim 2, wherein coal ash and beer yeast diatomaceous earth are ground into an average granularity of about 1 to 12 μm.

11. A ship bottom paint additive as recited in claim 2, wherein coal ash is ground into an average granularity of about 2–4 μm, and beer yeast diatomaceous earth is ground into an average granularity of about 3–10 μm.

12. A ship bottom paint additive as recited in claim 2, further comprising diatomaceous earth.

13. A ship bottom paint containing a ship bottom paint additive which comprises a mixture of coal ash and beer yeast diatomaceous earth, wherein the weight ratio of coal ash to beer yeast diatomaceous earth is within the range of about 3:1 to 7:1.

14. A ship bottom paint as recited in claim 13, wherein the coal ash comprises fly ash.

15. A ship bottom paint as recited in claim 13, wherein the beer yeast diatomaceous earth is in dry powder form.

16. A ship bottom paint as recited in claim 13, wherein coal ash and beer yeast diatomaceous earth are ground into an average granularity of about 1 to 12 μm.

17. A ship bottom paint as recited in claim 13, wherein coal ash is ground into an average granularity of about 2–4 μm, and beer yeast diatomaceous earth is ground into an average granularity of about 3–10 μm.

18. A ship bottom paint as recited in claim 13, further comprising diatomaceous earth.

19. A ship bottom paint containing a ship bottom paint additive which comprises a mixture of coal ash and beer yeast diatomaceous earth, wherein the ship bottom, paint additive is comprised of about 2.25–10% by weight coal ash and about 0.375–5% by weight beer yeast diatomaceous earth.

20. A ship bottom paint as recited in claim 19, wherein the coal ash comprises fly ash.

21. A ship bottom paint as recited in claim 19, wherein the beer yeast diatomaceous earth is in dry powder form.

22. A ship bottom paint as recited in claim 19, wherein coal ash and beer yeast diatomaceous earth are ground into an average granularity of about 1 to 12 μm.

23. A ship bottom paint as recited in claim 19, wherein coal ash is ground into an average granularity of about 2–4 μm, and beer yeast diatomaceous earth is ground into an average granularity of about 3–10 μm.

24. A ship bottom paint as recited in claim 19, further comprising diatomaceous earth.

25. A ship bottom paint additive which comprises a mixture of allophane and yeast.

26. A ship bottom paint additive which comprises a mixture of allophane, derived from coal ash, and yeast, derived from beer yeast diatomaceous earth.

* * * * *

UNITED STATES PATENT AND TRADEMARK OFFICE
CERTIFICATE OF CORRECTION

| | | |
|---|---|---|
| PATENT NO. | : 7,048,788 B2 | Page 1 of 1 |
| APPLICATION NO. | : 10/913133 | |
| DATED | : May 23, 2006 | |
| INVENTOR(S) | : Yamazaki et al. | |

It is certified that error appears in the above-identified patent and that said Letters Patent is hereby corrected as shown below:

On the title page

Item 57

Line 6 "mixture may" should read --mixture that may--

In the Claims

Col. 8, line 33 "bottom, paint" should read --bottom paint--

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,048,788 B2  Page 1 of 1
APPLICATION NO. : 10/913133
DATED : May 23, 2006
INVENTOR(S) : S. Yamazaki et al.

It is certified that error appears in the above-identified patent and that said Letters Patent is hereby corrected as shown below:

Title Page, item (54) and Col. 1 in specification:

| COLUMN | LINE | ERROR |
|---|---|---|
| 1 | Title | "SHIP BOTTOM PAINT USING COAL ASH AND DIATOMACEOUS EARTH" should read --SHIP BOTTOM PAINT ADDITIVE USING COAL ASH AND DIATOMACEOUS EARTH-- |
| 1 | Title | "SHIP BOTTOM PAINT USING COAL ASH AND DIATOMACEOUS EARTH" should read --SHIP BOTTOM PAINT ADDITIVE USING COAL ASH AND DIATOMACEOUS EARTH-- |

Signed and Sealed this

First Day of December, 2009

David J. Kappos
*Director of the United States Patent and Trademark Office*